United States Patent
Volyanskyy et al.

(10) Patent No.: US 10,832,799 B2
(45) Date of Patent: Nov. 10, 2020

(54) MULTI-LEVEL ARCHITECTURE OF PATTERN RECOGNITION IN BIOLOGICAL DATA

(71) Applicant: KONINKLIJKE PHILIPS N.V., Eindhoven (NL)

(72) Inventors: Konstantin Volyanskyy, Larchmont, NY (US); Nevenka Dimitrova, Pelham Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 290 days.

(21) Appl. No.: 15/749,694

(22) PCT Filed: Aug. 12, 2016

(86) PCT No.: PCT/EP2016/069308
§ 371 (c)(1),
(2) Date: Feb. 1, 2018

(87) PCT Pub. No.: WO2017/029249
PCT Pub. Date: Feb. 23, 2017

(65) Prior Publication Data
US 2018/0225414 A1    Aug. 9, 2018

Related U.S. Application Data

(60) Provisional application No. 62/205,778, filed on Aug. 17, 2015.

(51) Int. Cl.
| G06F 16/00 | (2019.01) |
| G16B 40/00 | (2019.01) |
| G06F 16/22 | (2019.01) |

(52) U.S. Cl.
CPC ......... G16B 40/00 (2019.02); G06F 16/2282 (2019.01)

(58) Field of Classification Search
CPC ........................... G16B 40/00; G06F 16/2282
See application file for complete search history.

(56) References Cited

U.S. PATENT DOCUMENTS

| 8,195,734 B1 * | 6/2012 | Long ..................... G06F 16/285 |
| | | 708/520 |
| 2003/0009470 A1 | 1/2003 | Leary |

(Continued)

FOREIGN PATENT DOCUMENTS

| EP | 2444914 A2 | 4/2012 |
| WO | 0156216 A2 | 8/2001 |

OTHER PUBLICATIONS

Wang, et al., "Fuzzy C-means method with empirical mode decomposition for clustering microarray data", Bioinformatics and Biomedicine, 2010 IEEE International Conference, Dec. 18, 2010, pp. 192-197.

(Continued)

*Primary Examiner* — Tarek Chbouki (57) ABSTRACT

Methods, systems and apparatus for detecting patterns in constituents of at least one biological organism are disclosed. In accordance with one method, clusters of the constituents are determined (208) by selecting (210) different subsets of at least one of genes or proteins and identifying (212) the clusters from biological data corresponding to the selected subsets. Here, membership values for the constituents, indicating membership within the clusters, are calculated for use as a basis of an additional cluster determination process (208) to obtain final clusters of constituents. By underpinning the preliminary clustering on different subsets of biological data and formulating the higher-level clustering on the basis of the membership values, the embodiments can enable an evaluation of a large variety of biological data in a practical, accurate and highly efficient manner.

20 Claims, 5 Drawing Sheets

(56) References Cited

U.S. PATENT DOCUMENTS

| | | | | |
|---|---|---|---|---|
| 2003/0028504 A1* | 2/2003 | Burgoon | ............... | G06K 9/6217 |
| 2011/0246080 A1* | 10/2011 | Polouliakh | ............ | G16B 40/00 |
| | | | | 702/19 |
| 2013/0077837 A1* | 3/2013 | Gobinet | ............... | G06K 9/6221 |
| | | | | 382/128 |
| 2014/0143251 A1 | 5/2014 | Wang et al. | | |
| 2014/0201126 A1* | 7/2014 | Zadeh | .................. | A61B 5/4803 |
| | | | | 706/52 |
| 2015/0213115 A1 | 7/2015 | Mukherjer et al. | | |

OTHER PUBLICATIONS

Fu, et al., "FLAME, a novel fuzzy clustering method for the analysis of DNA microarray data", BMC Bioinformatics, Biomed Central, London, GB, vol. 8, No. 1, Jan. 4, 2007, 15 pages, pages 1-15.

Berget, et al., "New modifications and applications of fuzzy C-means methodology", Computational Statistics and Data Analysis Elsevier Science B.V. Netherlands, vol. 52, No. 5, Jan. 20, 2008, pp. 2403-2418.

Chalise, et al., "Integrative clustering methods for high-dimensional molecular data", Transl Cancer Res, vol. 3, No. 3, Jan. 1, 2014, pp. 202-216.

Ben-Dor, et al., "Clustering Gene Expression Patterns", Journal of Computational Biology, 1999, pp. 33-42 (Abstract).

* cited by examiner

MULTI-LEVEL ARCHITECTURE OF PATTERN RECOGNITION IN BIOLOGICAL DATA

TECHNICAL FIELD

The present invention is directed generally to bioinformatics technology. More particularly, various inventive methods, systems and apparatus disclosed herein relate to pattern recognition in biological data.

BACKGROUND

Bioinformatics technology provides an efficient means for analyzing biological organisms and is an important aspect of several biological fields. In particular, bioinformatics technological processes have led to significant advancements in genomics and the study and treatment of diseases, including cancer. Cancer, as well as other genome diseases, are characterized by heterogenic patterns of genomic structural variations and gene expression underpinning the evolution from normal to tumor cells. For purposes of clinical studies, the ability to interpret and characterize distinctive patterns from available genomic data gains high importance. Various known and commercially available genomic technologies that can provide prognosis and risk assessment with respect to genome diseases include OncotypeDX, Genomic Grade Index, MammaPrint.

SUMMARY

The effectiveness of the currently available genomic technologies discussed above is relatively limited because the analyses employed by these technologies are generally based on a single set of genes. In particular, the dependence on a fixed, single set of genes renders these methods stagnant, as they do not address the evolving nature of genome diseases, such as cancer. Thus, while the gene signatures of these methods may have been effective in detecting particular subtypes of a disease, they will likely be ineffective in detecting newly developed subtypes due to the altered genomic characteristics arising from the evolution of the disease.

The present disclosure is directed to methods, systems and apparatus for detecting patterns in biological data. Exemplary embodiments described herein can provide an improvement over existing bioinformatics technology, as they can adapt to genomic characteristics of newly evolved subtypes of diseases. Specifically, the embodiments need not be dependent on a single, fixed set of genes or proteomic data, but can be configured to consider a wide variety of biological data, including, for example, copy number variation data, gene expression data and/or gene methylation data, for different sets of genes. Here, the embodiments can be configured to employ a multi-level architecture that variably selects different subsets of biological data, such as biological data for various sets of genes and/or proteomic data, for example, as predictive features and detects clusters of samples from which the data was compiled based on the features. Further, the embodiments can perform one or more additional, iterative levels of clustering in which the predictive features are composed of membership values indicating membership, or probabilities of membership, of the samples within the previously detected clusters. By underpinning the preliminary clustering on different subsets of biological data and formulating the higher-level clustering on the basis of the membership values, the embodiments can enable fluid evaluation of a large variety of biological data in a practical, accurate and highly efficient manner, thereby providing an effective means for adapting to the evolving nature of genome diseases.

Generally, in one aspect, an exemplary method for detecting patterns in constituents of at least one biological organism includes compiling a first feature data set from at least one of genomic or proteomic data of the constituents of the one or more biological organisms. In addition, clusters of the constituents are determined by selecting different subsets of at least one of genes or proteins and identifying the clusters from portions of the first feature data set corresponding to the selected subsets. Here, the determination of the clusters comprises computing membership values for the constituents indicating membership within the clusters. Further, an additional cluster determination process is performed to obtain final clusters of constituents, where the additional cluster determination process clusters the constituents based on the membership values. As indicated above, the selection of different subsets of genes and/or proteins improves the ability of the method to adapt to variances in the biological data stemming from the evolution of a disease. In addition, the selection of different subsets also improves the ability of the method to cluster several different types of biological data. At the same time, performing the additional cluster determination process on the basis of the membership values substantially improves the method's efficiency, while maintaining accuracy, thereby permitting the method to efficiently process a wide range of biological data in a practical manner.

In accordance with one embodiment, the performing of the additional cluster determination process includes identifying second clusters of the constituents from a second feature data set that is composed of at least a portion of the first membership values and computing second membership values for the constituents indicating membership within the second clusters. The iteration of the cluster determination process can improve the delineation and detection of the most relevant clusters.

In one version of the embodiment, the performing of the additional cluster determination process includes selecting different subsets of the first membership values and performing a cluster determination sub-process for each of the different subsets of the first membership values to obtain the second clusters. Thus, different clusters based on different subsets of the first membership values can be formed and evaluated. This aspect can also improve the adaptability of the method to variances in biological data.

Further, in accordance with one optional feature, the determining of the clusters of the constituents comprises forming the second feature data set by determining degrees of redundancy between clusters of the first clusters and pruning the membership values of at least one corresponding cluster of the first clusters having a respective degree of redundancy that is above a threshold. Evaluating the degree of redundancy in this way can improve the efficiency and accuracy of the method, as it can remove redundant clusters and corresponding biological data from consideration.

In accordance with one version of the embodiment, the performance of the additional cluster determination process can be iterated to obtain the final clusters, where each iteration of the performing comprises identifying other clusters of the constituents from an additional feature data set that is composed of at least a portion of preceding membership values determined from a preceding execution of the performance of the additional cluster determination process. As noted above, the iteration of the cluster determination process can improve the delineation and detection of the most relevant clusters, while the use of the membership values can improve the efficiency of the method.

Further, according to an exemplary embodiment, the membership values denote probabilities of membership to corresponding clusters. This aspect can provide improved flexibility, as it permits a given sample to be assigned to more than one cluster throughout the process.

In addition, in exemplary embodiments, a representation of at least one of the final clusters or the subsets of the genes and/or proteins denoting the final clusters can be displayed. Moreover, the representation can include at least one of clinical or phenotypic annotations to the final clusters to aid a clinician in assessing the data. In one version of the embodiment, the annotations include at least one of drug response data, risk of recurrence of a disease or disease subtype data.

Exemplary embodiments can further include providing diagnostic information. For example, in accordance with one method, each of the final clusters is associated with at least one of clinical variables, clinical outcomes or clinical labels. In addition, the method includes receiving at least one biological data sample and searching for at least one match to the biological data sample by comparing the sample to representations of the final clusters. Moreover, any one or more of clinical variables, clinical outcomes or clinical labels associated with a representation of at least one of the final clusters matching the sample is output as diagnostic information. Here, the diagnostic information can serve as a guide for a health care provider in diagnosing or prescribing a particular treatment to a patient. For example, the diagnostic information can indicate a particular cancer subtype from which a patient may be suffering. In addition, the diagnostic information can indicate that one or more particular drugs was successful or unsuccessful in treating a disease or ailment in patients of a cluster matching the biological data sample. As noted above, due to the flexibility and adaptability afforded by the embodiments described herein, a wide variety of diagnostic information can be provided.

Furthermore, in one aspect, a computer-readable medium comprises a computer-readable program that, when executed on a computer, enables the computer to perform any one or more of the methods described herein. For example, the computer-readable program can be configured to detect patterns in constituents of at least one biological organism such that, when the program is executed on a computer, the program causes the computer to perform the steps of any one or more of the method embodiments described herein. The computer-readable medium can be a computer-readable storage medium or a computer-readable signal medium. Alternatively or additionally, the computer readable medium can include an update or other portion of the computer-readable program.

As used herein for purposes of the present disclosure, the term "constituents of at least one biological organism" should be understood to include, but is not limited to, cells, cell lines, bacterial cultures, other microorganisms or patients.

The term biological data should be understood to include, but is not limited to, genomic data, including, for example, one or more of mutations, genome-wide copy number alterations, gene and/or noncoding RNA expression data, DNA methylation data, histone modifications, DNA binding data (e.g. ChIPseq), and/or RNA binding data, and/or other types of genomic data, proteomic data, including, for example, protein expression data, phosphorylation data, ubiquitination data and/or acetylation data of a biological sample, glucose level data, blood pressure data, weight data, body mass index (BMI) data, dietary data, and/or daily calorie intake, in addition to other types of biological data.

The term "controller" is used herein generally to describe various apparatus relating to the operation of computing devices. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein, and/or employs dedicated hardware. A controller may be implemented with or without employing a processor, and also may be implemented as a combination of dedicated hardware to perform some functions and a microprocessor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more computer-readable storage mediums (generically referred to herein as "memory," e.g., volatile and non-volatile computer memory such as RAM, PROM, EPROM, and EEPROM, floppy disks, compact disks, optical disks, magnetic tape, etc.). In some implementations, the storage mediums may be encoded with one or more programs that, when executed on one or more processors and/or controllers, perform at least some of the functions discussed herein. Various storage mediums may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers. In some implementations, computer readable signal mediums may be encoded with one or more programs that, when executed on one or more processors and/or controllers, perform at least some of the functions discussed herein. For example, a signal medium can be an electromagnetic medium, such as a radio frequency medium, and/or an optical medium, through which a data signal is propagated.

The term "addressable" is used herein to refer to a device (e.g., a controller or processor) that is configured to receive information (e.g., data) intended for multiple devices, including itself, and to selectively respond to particular information intended for it. The term "addressable" often is used in connection with a networked environment (or a "network," discussed further below), in which multiple devices are coupled together via some communications medium or media.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Current bioinformatic technologies for performing prognosis of genomic diseases rely on a single, static genomic signature. These technologies cannot guarantee capturing of the complete genomic profile of an individual patient, are costly, and make no beneficial use of additional genomic information such as, for example, DNA copy number data and/or DNA methylation data. As a result, a large amount of important genomic information that can be of beneficial use to the clinical community is discarded. Furthermore, application of those methods is restricted to specific subgroups of patients based on various factors, such as, for example, stage and lymph node status. Thus, these technologies disregard vast volumes of available genomic information without proper assessment of its utility and representation to clinicians. Moreover, due to the relatively rapid evolving nature of genomic diseases, these technologies may be ineffective in analyzing newly developing patterns in subtypes of these diseases.

In view of the foregoing, various embodiments and implementations of the present invention are directed to methods, systems and apparatus for detecting patterns in constituents of at least one biological organism. In particular, embodiments of the present invention can provide an improvement over existing bioinformatics technology by adapting to genomic or proteomic patterns of newly developed subtypes of genomic diseases. Thus, embodiments of the present invention need not rely on a single, fixed set of genomic or proteomic signatures to detect the presence or advancement of genomic diseases.

To provide an effective means for adapting to the evolving nature of genomic diseases, exemplary embodiments can implement a multilevel, hierarchical architecture for detecting cluster patterns in genomic or proteomic data. Specifically, on the first level of the hierarchy, embodiments can detect clusters of samples by variably selecting different subsets of a wide range of biological data as predictive features corresponding to different sets of genes and/or proteomic data. Moreover, on higher levels of the hierarchy, embodiments can perform iterative clustering procedures in which predictive features are composed of membership values indicating membership or probabilities of membership in previously detected clusters. By implementing the preliminary clustering on the basis of different subsets of biological data and performing the higher-level clustering on the basis of the membership values, the embodiments can adaptively evaluate a large variety of biological data in a very efficient and accurate manner.

The cluster patterns detected by exemplary embodiments can be effective in aiding health care practitioners in the diagnosis and treatment of diseases. For example, genomic and/or proteomic characteristics that distinguish clusters can be output or displayed to a practitioner to enable the health care practitioner to determine subtypes of genomic diseases present in the clusters. Alternatively or additionally, genomic/proteomic characteristics of the clusters can be pre-stored to enable the system to map the characteristics to those present in the cluster and annotate the clusters with clinical data labels corresponding to the pre-stored characteristics. Due to the adaptive nature of preferred embodiments, a very large variety of genomic diseases and corresponding characteristics can be analyzed by the exemplary methods and systems described herein. Other beneficial applications include testing the efficacy of a drug therapy treatment. Here, the identified cluster patterns and associated characteristics can enable a health care practitioner to determine whether a patient has responded well to therapy and provide the practitioner with information to permit her or him to decide whether to continue the treatment, or proceed with a new regimen.

In accordance with exemplary aspects, embodiments can incorporate all available genomic and/or proteomic information using a multi-level hierarchy of unsupervised/supervised learning methods aimed to extract important patterns in patient genomic/proteomic data without potential losses due to sole reliance on small gene subset. Embodiments can further provide a numerically efficient tool for its implementation. The tool can identify characteristic patterns in patient genomic data (e.g., gene expression, DNA copy number and methylation) and/or proteomic data and can improve over existing approaches in several ways. For example, exemplary embodiments can be configured to incorporate and consider all available genomic information, i.e. the entire genome. Moreover, exemplary embodiments can incorporate and consider different types of genomic and proteomic information. For example, the biological data analyzed by exemplary embodiments can comprise genomic data including, for example, mutations, genome-wide copy number alterations, gene and/or noncoding RNA expression data, DNA methylation data, histone modifications, DNA binding data (e.g. ChIPseq), and/or RNA binding data, in addition to other types of genomic data. Alternatively or additionally, clusters can be detected from proteomic data, which can be extracted from mass spectrometry methods and can be incorporated into the integrated analysis. Mertins et al., "Integrated proteomic analysis of post-translational modifications by serial enrichment," Nature Methods 10, 634-637 (2013), incorporated herein by reference, describes an example of a mass spectrometry method. The proteomic data can include protein expression data, phosphorylation data, ubiquitination data and/or acetylation data of a biological sample. Thus, by considering a wide range of biological data, exemplary embodiments can minimize the risk of losing important genomic information, can identify a broader range of patterns and can provide representations of the patterns and information to clinicians. In contrast, a single gene signature cannot represent several distinctive patterns. Further, it is generally not known, a priori, which signature may work reliably to represent the actual risk or condition. Accordingly, due to the flexibility inherent in preferred embodiments, a large variety of clinical inquiries can be effectively addressed, while at the same time providing a potentially significant cost reduction.

Exemplary method and system embodiments can identify patterns in various types of genomic/proteomic data in a combined or separate fashion to characterize patient data for clinical outcome prediction and subtyping. As indicated above, preferred embodiments can integrate and extract useful information from all available modalities of genomic and/or proteomic information, rather than reliance on a single subset of genes as is done in various known gene signature approaches. Exemplary system and method embodiments can be implemented as an efficient computational tool for genomic pattern recognition using a multilevel clustering architecture and a mechanism to link with supervised machine learning algorithms for data interpretation in a clinical context.

Figure 1:
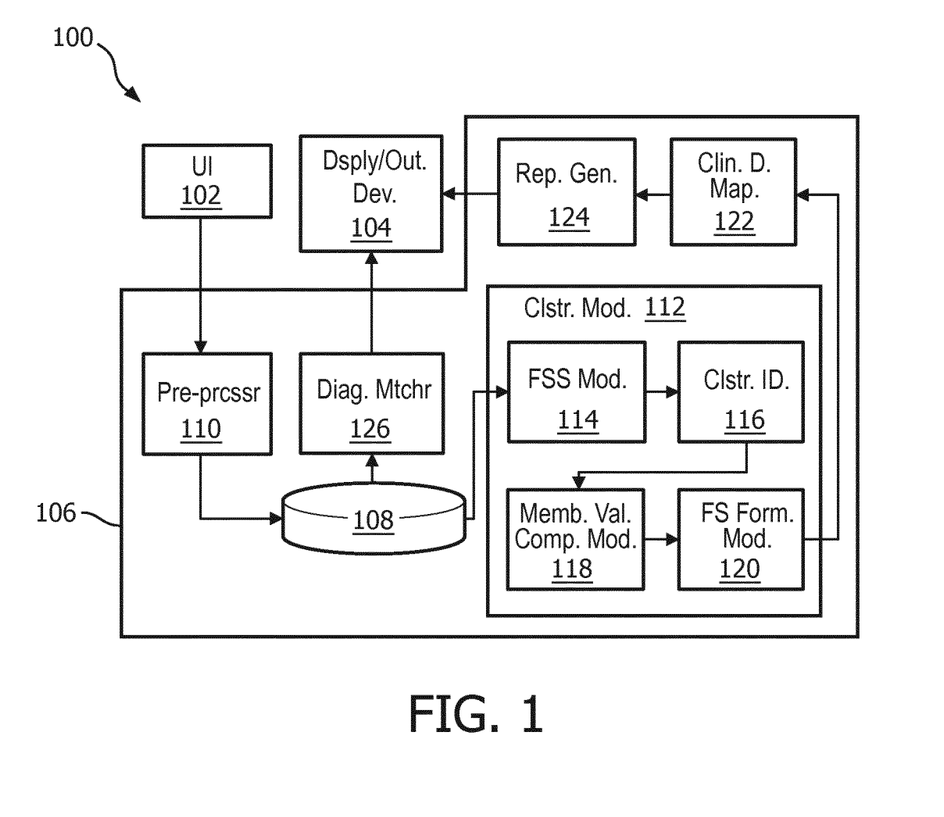
FIG. 1 is a high-level block/flow diagram of a system for detecting patterns in constituents of at least one biological organism in accordance with exemplary embodiments.

With reference now to FIG. 1, an exemplary system 100 system for detecting patterns in constituents of at least one biological organism in accordance with exemplary embodiments is illustratively depicted. The system 100 can include a pre-processor (Pre-prcssr) 110, a clustering module (Clstr. Mod.) 112, a clinical data mapper (Clin. D. Map.) 122, a representation generator (Rep. Gen.) 124, and a diagnostic matcher (Diag. Mtchr) 126. Each of the system components 110, 112, 122, 124 and 126 can be implemented by a controller (Cntrlr), which can be one or more hardware processors that are part of a hardware computing system 106. The computing system 106 can also include a storage medium 108, and the system 100 can include a user-interface (UI) 102 and a display/output device (Dsply/Out. Dev.) 104. In some embodiments, the user-interface and the display/output device 104 can be incorporated into a single device, such as, for example a touch-screen device. In addition, the clustering module 112 can include a feature set selection module (FSS Mod.) 114, a cluster identifier (Clstr. ID.) 116, a membership value computation module (Mem. Val. Comp. Mod.) 118 and a feature data set formulation module (FS Form. Mod.) 120. Exemplary functions of the various system components in accordance with exemplary embodiments are described herein below with respect to the method 200 of FIG. 2 and the method 400 of FIG. 4.

Figure 2:
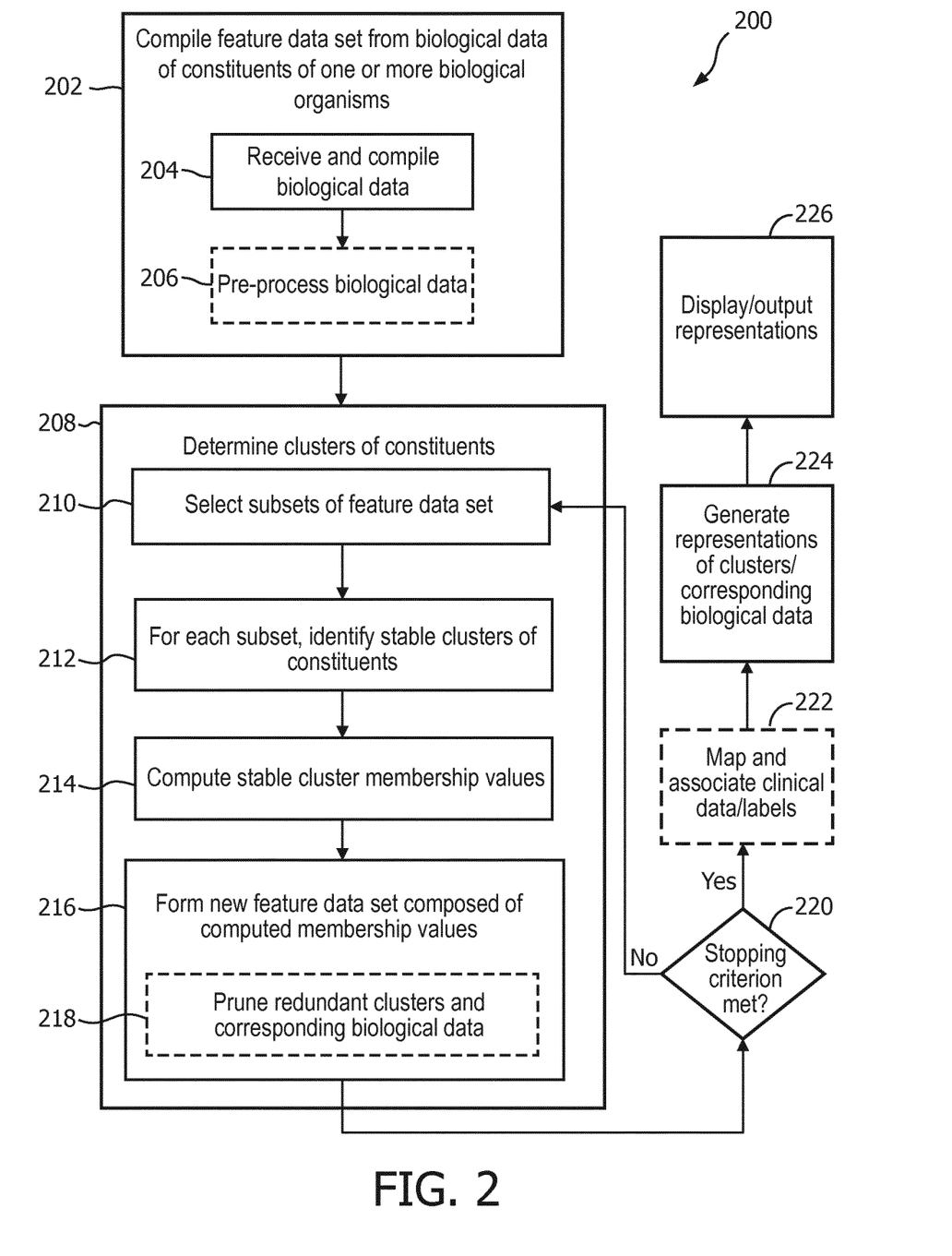
FIG. 2 is a high-level block/flow diagram of a method for detecting patterns in constituents of at least one biological organism in accordance with exemplary embodiments.

Referring to FIG. 2, with continuing reference to FIG. 1, an exemplary method 200 for detecting patterns in constituents of at least one biological organism is illustratively depicted. Here, the constituents can be cells, e.g., clonal cells, or cell lines of one or more organisms. Alternatively or additionally, the constituents can be the biological organisms themselves, including, for example, patients or even bacterial cultures. The method 200 can be applied to detect patterns in or of any one or more of these constituents based on biological data, which can include, for example, genomic data and/or proteomic data, compiled from the constituents. It should be noted that the methods 200 and 400 can be performed by the system 100 or 106. For example, the steps of the method 200, and the method 400, can be instructions of a program that can be stored on the storage medium 108 and executed by a controller implementing elements 110, 112, 122, 124 and/or 126, as, for example, discussed herein below.

The method 200 can begin at step 202, at which the pre-processor 110 can compile a feature data set from biological data of constituents of one or more biological organisms. For example, the pre-processor 110 can receive the biological data at step 204 and, in one embodiment, can directly compile the data in one or more matrices. The input data can also be received in the form of a data matrix or a set of data matrices, which can be merged or analyzed separately. For example, the method 200 can be performed for each of the data matrices in a set.

The biological data received and compiled at step 202 can include at least one of genomic data or proteomic data. For each member of the cohort, the genomic data can include, as discussed above, one or more of genome-wide copy number alterations, gene expression data, methylation data, and/or other types of genomic data. Alternatively or additionally, as noted above, proteomic data can include protein expression data, phosphorylation data, ubiquitination data and/or acetylation data of a biological sample. Proteomic data is the functional readout of the genomic architecture and many gene biological processes. The genomic and/or proteomic data may be composed of one of the types of data described above or any combination of the different types of data. The copy number alterations can denote deletions and amplifications for various regions of a genome for each member of the cohort. Gene expression data and methylation data represent additional types of genome characterization in terms of over/under expression of genes and degree of gene silencing or activation in a given biological organism. These data are provided as quantitative variables derived from measurement procedures and can be part of the input received at step 202. It should also be noted that although genomic and proteomic data are described here as examples, the biological data can additionally or alternatively include other types of data, as noted above. As understood by those skilled in the art based on the present Specification, the data can be formulated and analyzed in a manner similar to the examples described herein below with respect to genomic data.

It should be noted that, in addition to biological data, the user may optionally input annotations/labels, which can comprise clinical variables, clinical outcomes and/or other clinical labels, to the system 106 at step 202. The annotations/labels are discussed in detail herein below with respect to steps 222 and 224, and also method 400 depicted in FIG. 4.

At step 204, as indicated above, the pre-processor 110 can formulate the biological data compiled from the cohort of the constituents of the biological organism(s) as a matrix within at least one data structure of the storage medium 108. For example, genomic data compiled from the cohort can be formulated as follows:

$$\begin{matrix} CNA_{1,1} & \ldots & CNA_{M,1} & GE_{1,1} & \ldots & GE_{M,1} & M_{1,1} & \ldots & M_{M,1} \\ CNA_{1,2} & \ldots & CNA_{M,2} & GE_{1,2} & \ldots & GE_{M,2} & M_{1,2} & \ldots & M_{M,2} \\ CNA_{1,3} & \ldots & CNA_{M,3} & GE_{1,3} & \ldots & GE_{M,3} & M_{1,3} & \ldots & M_{M,3} \\ \vdots & \vdots & \vdots & \vdots & \vdots & \vdots & \vdots & \vdots \\ CNA_{1,N} & \ldots & CNA_{M,N} & GE_{1,N} & \ldots & GE_{M,N} & M_{1,N} & \ldots & M_{M,N} \end{matrix} \quad (1)$$

In this particular example, the genomic data consists of genome-wide copy number alteration (CNA), gene expression data (GE), methylation data (M). However, it should be understood that the matrix can be composed of one of these types of data or any sub-combination of these types of data or other types of data discussed above. Further, each set of columns denotes a particular member of a cohort, which can be, for example, a particular cell of a given patient, or a particular patient. For example, if the cohort members are patients, the patients are denoted by the first subscript in the elements of matrix (1), where $CNA_{1,m}$, $GE_{1,m}$ and $M_{1,m}$ denote copy number alteration data, genome expression data and methylation data of patient 1, $CNA_{2,m}$, $GE_{2,m}$ and $M_{2,m}$ denote copy number alteration data, genome expression data and methylation data of patient 2, etc. Here, m denotes an arbitrary chromosome region of a genome, where the genome of each patient in the cohort is delineated by 1, 2, 3 . . . N regions along the genome length. The delineated regions are denoted by the rows in Matrix (1). For example, $CNA_{1,1}$, $GE_{1,1}$ and $M_{1,1}$ denote copy number alteration data, genome expression data and methylation data, respectively, of region 1 of patient 1, $CNA_{1,2}$, $GE_{1,2}$ and $M_{1,2}$ denote copy number alteration data, genome expression data and methylation data, respectively, of region 2 of patient 1, $CNA_{2,2}$, $GE_{2,2}$ and $M_{2,2}$ denote copy number alteration data, genome expression data and methylation data, respectively, of region 2 of patient 2, etc. Thus, $CNA_{1,m}$ can denote a normal alternation, a deletion or an amplification in region m of the genome of patient n, while $GE_{n,m}$ can denote values of genes that are expressed at region m of the genome of patient n. The delineated regions of the genome can also be received at step 202 and subsequently arranged as a column vector, which can be stored in a storage structure within the storage medium 108 and can be a reference employed by any one or more of the elements of the system 106 to map elements of matrix (1) to particular genome regions. Thus, in matrix (1), each column can denote a different patient in the cohort, where the first subscript in any matrix element denotes a particular patient in the cohort, and each region 1, 2, 3 . . . N corresponds to the genomic data for that patient.

In accordance with one embodiment, the matrix (1) can be the feature data set compiled in step 204. Alternatively, the matrix (1) can be further pre-processed to obtain a feature data set that is analyzed in step 208 and subsequent steps. For example, optionally, at step 206, the pre-processor 110 can perform data centering, normalization and/or outlier detection on the data received and compiled at step 204. Here, to perform data centering, the pre-processor 110 can compute and subtract mean values in the feature vectors as follows:

$$X := X - M(X) \quad (2)$$

where X is the feature vector, which can be matrix (1), a column of matrix (1) or a set of columns in matrix (1), and M(X)=Average(X).

Further, to perform data normalization, the pre-processor 110 can employ a transformation that is most appropriate for the specific data type. For example, the pre-processor 110 can implement the normalization by performing one of the following procedures. In accordance with a first procedure, the pre-processor 110 can divide each feature vector by the maximum element as follows:

$$X := X / MAX(X) \quad (3)$$

where X is the feature vector, which can be matrix (1), a column of matrix (1) or a set of columns in matrix (1), and MAX(X) is the maximum element in the feature vector X. In a second procedure, the pre-processor 110 can compute the standard deviation and divide each feature vector by a respective standard deviation as follows:

$$X := X / STD(X) \quad (4)$$

where X is the feature vector, which can be matrix (1), a column of matrix (1) or a set of columns in matrix (1), and STD(X) is the standard deviation of the feature vector X. In accordance with the third procedure, the pre-processor 110 can compute each feature range and can divide the feature vector by the range length as follows:

$$X := X / LENGTH(RANGE(X)) \quad (5)$$

where X is the feature vector, which can be matrix (1), a column of matrix (1) or a set of columns in matrix (1), and RANGE(X) is the range of values in the feature vector, and LENGTH(RANGE(X)) is the length of the range.

Further, to perform outlier detection, at optional step 206, the pre-processor 110 can identify outliers in the biological data received at step 204 and can separate the outliers from the biological data. Thus, the feature data set compiled by the pre-processor 110 at step 202 can be the centralized and normalized data set without any identified outliers. For example, to determine and separate outliers, the pre-processor 110 can apply one or more of a variety of approaches, including at least one of a Mahalanobis distance method or a principal component analysis (PCA) method. Here, the pre-processor 110 can apply one of these methods, both of the methods or any sub-combination of these methods with any appropriate method that identifies and separates outliers.

For each of these methods, the biological data received at step 204 can be composed in a data matrix.

In the Mahalanobis distance method, the pre-processor 110 can split the data matrix, which would typically have a high dimension, into regions. Here, each data category can be grouped in the matrix, as, for example, adjacent columns. For example, genome-wide copy number alteration data can be grouped in a set of adjacent columns, gene expression data can be grouped in a set of adjacent columns, methylation data can be grouped in a set of adjacent columns, etc. The pre-processor 110 splits the matrix such that each category set is split into multiple regions, so that any given region is composed of data from only one category. For each region and data category, the pre-processor 110 can compute a mean value estimate M(X) and a covariance estimate C(X) as follows:

$$M(X)=\text{Average}(X) \quad (6)$$

$$C(X) = \frac{1}{n-1} \sum (x - M(X))^T (x - M(X)) \quad (7)$$

where X denotes a data category, which can be, for example, a copy number alteration category, a gene expression data category or a methylation data category, x denotes a value or element in the region, and n here denotes the number of elements in the region. The pre-processor 110 can compute the Mahalanobis distance MD(x, X) for each element x in quadratic form as follows:

$$MD(x, X)=(x-M(X))C^{-1}(X)(x-M(X)) \quad (8)$$

Further, the pre-processor 110 can detect outliers as points with large Mahalanobis distances that are above a threshold. The signal formulation module 112 can also evaluate the Mahalanobis distances using a chi-squared ($\chi^2$) distribution of degrees of freedom identified from the region dimension (n-1).

In the PCA analysis method, the pre-processor 110 can linearly transform (rotate) the original data matrix such that the correlation matrix is diagonalized in the transformed space. Here, the pre-processor 110 can split the correlation matrix into regions, as for example discussed above with regard to the Mahalanobis distance method, and can select the number of principal components based on the threshold of variance captured by these components. For example, the threshold can be chosen to be 90%. The pre-processor 110 can compute the Mahalanobis distance on the obtained principal components as discussed above with respect to equations 6-8 and can apply the chi-squared test to identify abnormally high values as outliers, as discussed above.

At optional step 206, the pre-processor 110 can further pre-process the biological data by filtering the data based on variance of features across samples. Here, the pre-processor 110 can filter raw data received through the user-interface 102, the matrix (1), or the compiled data resulting from data centering, normalization and/or outlier detection discussed above. The processor 110 can filter the data features by evaluating variance across samples and applying minimum variance threshold. Specifically, the processor 110 can compute variance for each feature across all samples, and can exclude features in response to determining that their variance falls below a q percentile. The value of q can be defined by the properties of the computed variance distribution. In accordance with one exemplary embodiment, the pre-processor 110 can set q to 75%.

In accordance with exemplary embodiments, the preliminary feature data set can be composed of data resulting from step 206, or step 204. After compiling the feature data set at steps 204 and/or 206, the pre-processor 110 can store the feature data set within a data structure in the storage medium 108 for subsequent retrieval by the clustering module 112, or can prove the feature data set directly to the clustering module 112.

At step 208, the clustering module 112 can determine clusters of the constituents. In accordance with preferred embodiments, the clustering can be implemented by performing steps 210-216, as discussed herein below. At step 210, the feature set selection module 114 can select subsets of the feature data set. For example, the feature set selection module 114 can select different subsets of at least one of genes or proteins. In accordance with one example, all gene and/or proteomic data features of all available types (e.g., gene expression, copy number, methylation, protein expression data, phosphorylation data, etc.) are split into small-sized groups or subsets by performing an iterative sampling procedure. Here, for purposes of simplifying calculation, each group/subset can be composed of data from only one type. For example, the feature set selection module 114 can select subsets composed of gene expression data, subsets composed of copy number data, subsets composed of methylation data, subsets composed of protein expression data, subsets composed of phosphorylation data, etc. The subsets/groups can be composed of any of the types of genomic and/or proteomic data discussed above. Further, step 208 can be performed separately, optionally in parallel, for each type of data, such as, for example, methylation data, gene expression data and copy number data. Here, the stopping criterion at step 220, discussed herein below, can also be applied separately and in parallel for each type of data.

In accordance with exemplary embodiments, the feature set selection module 114 can randomly select the subsets of data. For example, during the sampling procedure, the feature set selection module 114 can select a gene subset GS1={A, B, C, D, E, F, G, H, I, J}, gene subset GS2={A, B, K, L, M, N}, etc., where each component, e.g., A, B, C, D . . . , corresponds to genomic data from a particular chromosome region or gene. For example, using the notation employed to describe the matrix 1, the components can be copy number data $CNA_{n,A}$, $CNA_{n,B}$, $CNA_{n,C}$, $CNA_{n,D}$, etc., where n denotes a particular constituent, which, as noted above, can be a patient, and A, B, C, D, . . . etc. denotes a chromosome region or gene. Similarly, the components of the subset can be gene expression data, e.g., $GE_{n,A}$, $GE_{n,B}$, $GE_{n,C}$, $GE_{n,D}$, etc., methylation data, $M_{n,A}$, $M_{n,B}$, $M_{n,C}$, $M_{n,D}$, etc., or any other type of genomic and/or proteomic data discussed above. For expository purposes, the method is described herein below with respect to gene expression data. However, it should be understood that the method can be readily applied to other types of genomic and/or proteomic data as understood by those of ordinary skill in the technical field based on the present Specification.

At step 212, for each of the selected subsets, the cluster identifier 116 can identify stable clusters of constituents. For example, the cluster identifier 116 can identify the clusters from portions of the first feature data set corresponding to the selected subsets. In accordance with exemplary embodiments, a fuzzy clustering procedure can be applied to each subset of features to thereby identify stable clusters. However, it should be understood that, in accordance with other exemplary embodiments, clustering methods that are different than those specifically described herein can be applied at step 212. One exemplary fuzzy clustering procedure that can be performed at step 212 is a Fuzzy C-means clustering procedure. Here, the cluster identifier 116 can determine the clusters by minimizing the following function:

$$\operatorname*{argmin}_{C} = \sum_{i=1}^{n} \sum_{j=1}^{c} w_{i,j}^{m} \|s_i - c_j\|^2 \quad (9)$$

where $S=\{s_1, \ldots, s_n\}$ is a set of subsets for a given type of genomic or proteomic data determined at step 210, $C=\{c_1, \ldots, c_c\}$ is a set of c cluster centers, where each cluster center denotes a particular cluster, $w_{i,j}$ is a set of membership values, for $i=1, \ldots, n$ $j=1, \ldots, c$, that are between 0 and 1 indicating the probability with which a corresponding subset $s_i$ is a member of cluster $c_j$, and m is a degree of fuzzification. The set S of subsets can, as discussed above, be composed of gene subsets GS1, GS2, etc. Further, the membership function can be formulated as follows:

$$w_{i,j} = \frac{1}{\sum_{k=1}^{c} \left( \frac{\|s_i - c_j\|}{\|s_i - c_k\|} \right)^{\frac{2}{m-1}}} \quad (10)$$

Moreover, the cluster centers $c_j$ can be denoted as follows:

$$c_j = \frac{\Sigma_s w_k(s)^m s}{\Sigma_s w_k(s)^m} \quad (11)$$

where $w_k$ is the membership function (10) for the subset s. In accordance with preferred embodiments, the degree of fuzzification is set to 2; however, it should be understood that other fuzzification levels can be employed. In addition, the cluster identifier 116 can determine the number of clusters c by applying, for example, the F-test, in which a ratio of group variance to total variance is calculated and plotted against the total number of clusters. The cluster identifier 116 can select the number of clusters c as the cutoff value at which the ratio is essentially consistent for the numbers of clusters greater than the cutoff value. For example, the cutoff value can be the value of the number of clusters at which the ratio does not change more than 5%. However, it should be noted that other methods of determining the number of clusters can be applied. Alternatively, the number of clusters c can be liberally selected as a pre-set value that is stored in the storage medium 108 and employed by the cluster identifier 116 to perform step 212. To implement the clustering procedure, the cluster identifier 116 can randomly select the preliminary values of the membership function, and iteratively solve (9) until convergence, i.e. until the membership functions do not change beyond a threshold between iterations, to determine the cluster centers (11).

At step 214, the computation module 118 can compute membership values for each of the constituents. For example, the computation module 118 can compute the stable cluster membership values by solving (10) above using the cluster centers determined at step 212. Accordingly, each data sample, or constituent, is correlated to the determined clusters with an associated cluster membership value. As a result, given the original data matrix of dimension N×M for a given data type, where M=number of samples, or patients, and N=number of features, the clustering module can obtain a reduced data matrix of dimension M×q, where $q=q_1+q_2+ \ldots +q_L \ll M$ and where $q_i$ is the number of stable clusters identified from ith subset of features. In the example described herein below, q1 is 2 and q2 is 3 such that there are 5 stable clusters. The computation module 118 can also determine the stability of the clusters by using the Bootstrap method and assessing the changes in the Rand Index. Accordingly, the reduced data matrix can be composed of computed cluster membership values for each sample or constituent and every cluster. These class membership values can be further assessed as new features that are propagated to the next level of the computed clustering hierarchy, as discussed in more detail herein below.

For purposes of illustrating the clustering procedure discussed above, reference is now made to an example in which two gene subsets are selected at step 210, as discussed above. For example, the cohort of constituents can be composed of three patients, P1, P2, P3, and the gene subsets can be composed of two gene sets with corresponding gene expression values: GS1={A, B, C, D, E, F, G, H, I, J} and GS2={A, B, K, L, M, N}. In addition, cluster identifier 116 can perform step 212 by applying a fuzzy clustering procedure on gene set GS1 to identify two stable clusters CL1, CL2, and applying the fuzzy clustering procedure on gene set GS2 to identify three stable clusters CL3, CL4, CL5. In addition, for each patient and for every cluster, the computation module 118 can obtain associated class membership values or probabilities: $q_{ij} > 0$, as provided in the Table 1 below:

TABLE 1

| | Cluster Membership Functions | | | | |
|---|---|---|---|---|---|
| Patient | CL1 | CL2 | CL3 | CL4 | CL5 |
| P1 | $q_{11}$ | $q_{12}$ | $q_{13}$ | $q_{14}$ | $q_{15}$ |
| P2 | $q_{21}$ | $q_{22}$ | $q_{23}$ | $q_{24}$ | $q_{25}$ |
| P3 | $q_{31}$ | $q_{32}$ | $q_{33}$ | $q_{34}$ | $q_{35}$ |

Accordingly, instead of assessing gene expression values for 14 genes A, B, . . . ,N, the clustering module 112 can reduce the data space to 5 data points for each patient, namely the associated cluster membership functions or values. At the next level of analysis, the method can be repeated using the cluster membership values as the feature data set, as discussed in detail herein below. The procedure can continue iteratively until a stopping criteria is met, as discussed herein below.

At step 216, the feature set formulation module 120 can form a new feature data set composed of the computed membership values. For example, the formulation module 120 can formulate a new or second feature data set as a matrix composed of table 1. To maintain consistency with the data matrix (1), the rows of table 1 can be the columns of the new feature data set, and the columns of table 1 can be the rows of the new feature data set. In accordance with one exemplary aspect, the formulation module 120 can form the new or second feature data set by determining degrees of redundancy between clusters determined at step 212. Depending on the cluster separability properties, the formulation module 120 can propagate or discard a respective set of predictive features corresponding to a specific subset determined at step 210. Thus, within a small size feature set, the formulation module 120 can apply further filtering by discarding features with a low effect on cluster distribution.

For example, optionally, at step 218, the formulation module 120 can prune redundant clusters and corresponding biological data. Here, the formulation module 120 can prune different subsets of at least one of genes or proteins based on cluster redundancy computations. For example, in response to determining that the membership functions for two or more clusters are similar, the formulation module 120 can deem the clusters to be redundant. In addition, in response to determining that samples, constituents or patients are equally distributed between two clusters, then formulation module 120 can deem the clusters to be redundant. Thus, the formulation module 120 can prune or discard, and exclude from the new feature data set, the membership values of all but one of the redundant clusters. For example, the formulation module 120 can prune clusters that have a respective degree of redundancy that is above a threshold. The degree of redundancy can be, for example, the inverse of one or more distance measures such as a Euclidean distance measure, a Manhattan distance measure, etc. Accordingly, in response to determining that the inverse of the distance measure between membership functions or values of two or more clusters is above a threshold, the formulation module 120 can prune the membership values of all but one of the clusters. Equivalently, in response to determining that the distance measure between membership functions or values of two or more clusters falls below a corresponding threshold, the formulation module 120 can prune the membership values of all but one of the clusters. In some circumstances, pruning the membership values of redundant clusters essentially prunes the biological data from which the clusters were determined. For example, if clusters CL1 and CL2 in the example discussed above with respect to Table 1 are redundant with respect to CL3, then pruning the corresponding membership values of the clusters discards gene subset GS1. Similarly, assuming that more than two gene subsets were selected, if the formulation module 120 determines that any one of the clusters CL3, CL4 or CL5 in the example discussed above with respect to Table 1 are not redundant, then the formulation module 120 propagates the corresponding membership values in the new feature data set, which essentially propagates gene subset GS2.

At step 220, the clustering module 112 can determine whether a stopping criterion has been met. If not, then the method can proceed to step 210 and can be repeated. Otherwise, if the criterion has been met, then the method can proceed to step 222. The stopping criterion can be that number of iterations does not exceed specified maximum, and/or that the cluster separability, which can be measured as any one or more of the inter-cluster distances discussed above, does not improve over certain percentage (e.g., 5%) after N (e.g., N=100) consequent runs.

At step 208, proceeding from step 220, the clustering module 112 can perform an additional cluster determination process to obtain final clusters of constituents. Here, the additional cluster determination process clusters the constituents based on membership values determined at the preceding iteration of the step 208. For example, the clustering module 112 can perform step 208 as discussed above, except that, as opposed to using the feature data set determined at step 202, the clustering module 112 applies step 208 to the new or second feature data set determined at step 216 in the preceding iteration of step 208. Thus, at a second iteration of step 210, the selection module 114 can select different subsets of the membership values of the new or second feature data set. Further, at a second iteration of step 212, the cluster identifier 116 can identify second clusters of the constituents from the new or second feature data set as discussed above by using the subsets of membership values determined at step 210. For example, the cluster identifier 116 can perform a cluster determination sub-process, such as the fuzzy clustering procedure discussed above, for each of the different subsets of membership values to obtain the second clusters. Further, at step 214, the computation module 118 can compute second membership values for the constituents indicating membership within the second clusters. In addition, at step 216, the formulation module 120 can form a new feature data set composed of the second membership values. The formulation module 120 can, at optional step 218, prune redundant clusters and corresponding membership values, as discussed above.

The method can proceed to step 220 and, if the stopping criterion is not met, then the clustering module 112 can continue to iteratively perform step 208 to obtain the final clusters until the stopping criterion is met. Here, each iteration of the performance of the method 200 can comprise identifying other clusters of constituents from an additional or new feature data set that is composed of at least a portion of preceding membership values determined from a preceding execution of step 208. It should be noted that, because one or more of the membership values may be pruned at step 218, not all of the membership values determined at step 214 of a given iteration may be propagated for evaluation in the following iteration.

If, at step 220, the clustering module 208 determines that the stopping criterion is met, then the clustering module 208 can store in the storage medium 108 and/or output at step 226 the clusters determined at the most recent iteration of step 212 and/or the corresponding membership values determined at the most recent iteration of step 214 as the respective final clusters and/or final membership values. Accordingly, the final cluster representation can be based on the membership values derived across a series of clustering and sampling runs.

Optionally, at step 222, the clinical data mapper 122 can map and associate clinical data with the final clusters, and/or assign labels and/or annotations to the final clusters. For example, the annotations can include at least one of drug response data, risk of recurrence of a disease (e.g., low risk, medium risk, high risk, etc.) or disease subtype data. Annotations/labels can be received from a user through the user interface 102, stored in the storage medium 108, and correlated to the constituents of the cohort at step 202, discussed above. Based on the correlation, the clinical data mapper 122 can map the annotations/labels to the respective clusters. If the annotations/labels are not available, then the clinical data mapper can generate and assign annotations/labels to each computed final cluster. For example, the annotations/labels can be accessed from an outside database storing information about the biological data clustered in accordance with the method 200. The annotations/labels can indicate which patients received a certain drug, which patients responded well to the drug and which patients did not respond well to the drug to enable the health care practitioner determine whether the drug was effective. Thus, if the cluster representations indicate that the patient responded to the drug, then they can indicate to a health care practitioner that the treatment should continue. The annotations/labels can also include clinical or phenotypic data, including subtype data, which in turn can include specific types of cancer that are clinically relevant.

It should be understood that the annotations can include clinical variables, clinical outcomes and/or other clinical labels. For example, in accordance with exemplary aspects, at step 222, each cluster identified at step 208 can be assigned or associated with one or more clinical variables, clinical outcomes and/or other clinical labels. For example, a clinical variable can be one or more drugs administered to patients whose biological data was input at step 202, a prescribed diet followed by the patients, and/or a physical therapy regimen undergone by the patients, among other variables. The clinical variable can also include a disease or ailment that the drug, diet and/or physical therapy aimed to cure. In turn, the corresponding clinical outcome can be an indication of whether the drug, diet, physical therapy resulted in curing or improving the disease or ailment suffered by the patient. The clinical variables and clinical outcomes can be known a priori, before the clustering step 208 is performed. Here, at step 222, by referencing the correlation between patients/biological data and clinical variables and clinical outcomes, the clinical data mapper 122 can map the corresponding clinical variables/clinical outcomes to the clusters identified at step 208. For example, the subsets of feature data, such as GS1 or GS2, and the values of a centroid, or other mathematical representation, for a final cluster determined at step 212, can be mapped to the corresponding clinical variables and clinical outcomes of patients belonging to the respective final cluster, which can be patients that have a final membership value that is above a threshold, such as, for example 0.9. Further, the centroid can be the cluster center determined in accordance with equation (11) discussed above. For example, the representation generator 124 can formulate the representation as a matrix of proteins sets and/or gene sets, such as, for GS1 or GS2, and corresponding values denoting, for example, copy number alteration data, gene expression data, and/or methylation data for the set that form a centroid of the biological data of the constituent members of the corresponding final cluster determined at step 212. Here, the centroid representation, or other representation, along with the clinical variable/outcome annotations can serve as a model that can act as a guide for the clinical management of new patients, as discussed herein below. It should be noted that any type of annotation/label can be mapped to the respective cluster. For example, besides clinical variables and outcomes, the annotations/labels can be, for example, cancer subtype data. For example, like the clinical variables and outcomes, the clinical labels can be known a priori, before the clustering step 208 is performed. At step 222, by referencing the correlation between patients/biological data and clinical labels, the clinical data mapper 122 can map the corresponding clinical labels to the final clusters identified at step 208. For example, similar to the clinical variables and outcomes, the subsets of feature data, such as GS1 or GS2, and the values of the centroid, or other mathematical representation, for a final cluster determined at step 212, can be mapped to the corresponding label/subtype of patients belonging to the respective final cluster. The centroid/mathematical representation together with the clinical labels can be employed as a model for comparison purposes that can aid in the diagnosis of a patient. The labels can be any clinically relevant data including, for example, recurrence information, survival rate, mutation data for a specific gene or set of genes, expression level of a gene or expression levels of genes of a specific pathway, etc.

At step 224, the representation generator 124 can generate representations of the final clusters and/or representations of the corresponding biological data, including any data labels or annotations mapped or assigned at step 222, and store the generated representations within the storage medium 108. For example, each cluster representation can be a centroid, or another adequate representation, as discussed above with respect to step 222, for a final cluster for a corresponding subset of feature data. Alternatively, the representation of a cluster can be a combination of the centroid, or other adequate mathematical representation, and clinical variable/outcome data, clinical label, and/or other annotation mapped to the cluster at step 222. For example, one cluster representation can include a centroid of a cluster, an indication of the drug administered to patients belonging to the cluster, the disease or ailment that the drug treatment aimed to cure and an indication that the drug was successful. Similarly, another cluster representation can include a centroid of a different cluster, an indication of the same drug administered to patients belonging to the cluster, the corresponding disease or ailment and an indication that the drug was not successful. As discussed herein below, the cluster representations can serve as a model that can aid a healthcare provider in assessing whether a new patient will respond well to the drug. Alternatively, a cluster representation can include a centroid of a cluster and a cancer subtype label. Here, the cluster representation can be employed for comparison purposes to aid a health care provider in diagnosing the illness from which a patient is suffering. The computed patterns/representations are visualized and provided with clinical annotation for interpretation. For example, the representation can be a graph, heat map, or 2D plots, where points represent patients or other types of constituents. Further, the representation can include representations of the subsets genes or proteins denoting the final clusters. Here, the subsets can correspond to the genomic or proteomic data subsets upon which the final clusters were determined. For example, if clusters CL1 and CL2 in the example discussed above with respect to table 1 are among the final clusters, then the representation can include a representation of gene subset GS1.

At step 226, the representation generator 124 can direct the display/output device 104 to display or output the generated representations. As noted above, the representation can be a representation of at least one of the final clusters or the subsets genes or proteins denoting the final clusters. Further, at least one of clinical or phenotypic annotations to the final clusters can also be displayed.

Figure 3:
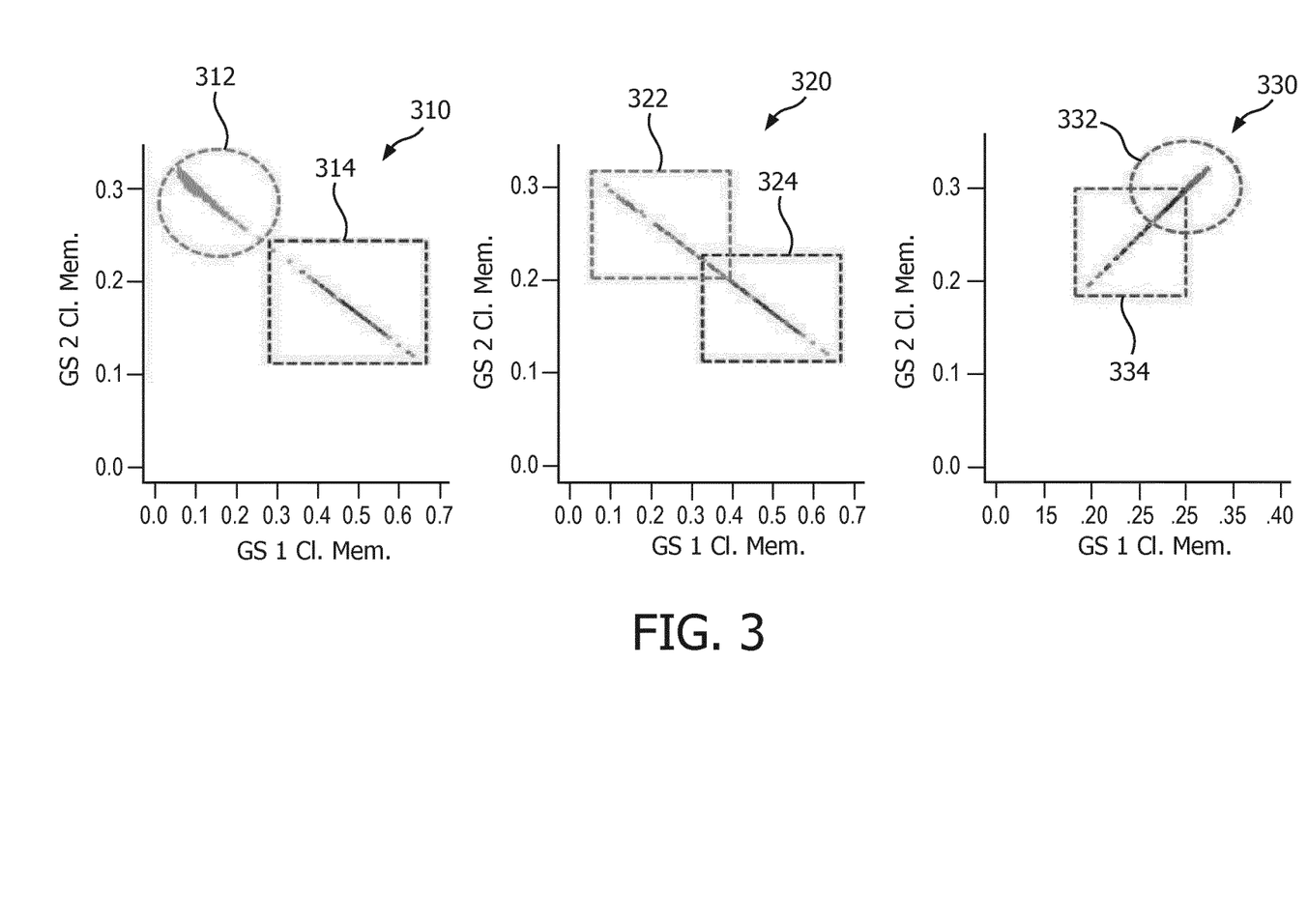
FIG. 3 is a diagram illustrating examples of cluster representations in accordance with exemplary embodiments.

For expository purposes, the method 200 was applied to perform subtype identification in 514 Breast Cancer patients from the Cancer Genome Atlas data repository. Here, Agilent microarray gene expression values for two sets of genes were employed as feature data in matrix (1) above. Two gene sets were selected in the method such that the first set of genes consisted of 16 genes, and the second set consisted of 17 genes. Further, the fuzzy clustering procedure discussed above was performed twice with a degree of fuzzification=2, and for each set of genes, the method identified four stable clusters. Specifically, the method computed cluster membership values for each of the initial clusters, and on the second iteration, the method identified new clusters using membership values from the initial clusters as new features, as discussed above. FIG. 3 illustrates exemplary representations that can be output/displayed at step 226. Here, cancer subtypes Basal, Lum (luminal) and Her2 were mapped to final clusters. Three subtypes are illustrated, as Lum is representative of two similar subtypes. In plots 310, 320 and 330, the vertical axis denotes gene set 2 class membership values (GS 2 Cl. Mem.), which is the probability of being (i.e., the membership values) in one cluster stemming from gene set 2, while the horizontal axis, gene set 1 class membership values (GS 2 Cl. Mem.), denotes the probability of being in another one of the three clusters stemming from gene set 1. Further, cluster 312 denotes a Lum cluster, cluster 314 denotes a Basal cluster, cluster 322 denotes a Her2 cluster, cluster 324 denotes a Basal cluster, cluster 332 denotes a Lum cluster and cluster 334 denotes a Her2 cluster. The representations illustrate a very good separation between Basal and Her2, Basal and Luminal subtypes. In this example, the representations indicate that Gene Set 2 is not as representative as Gene Set 1, however, combining the two gene sets eliminates insufficiencies of a predictive model based on Gene Set 1 only.

Figure 4:
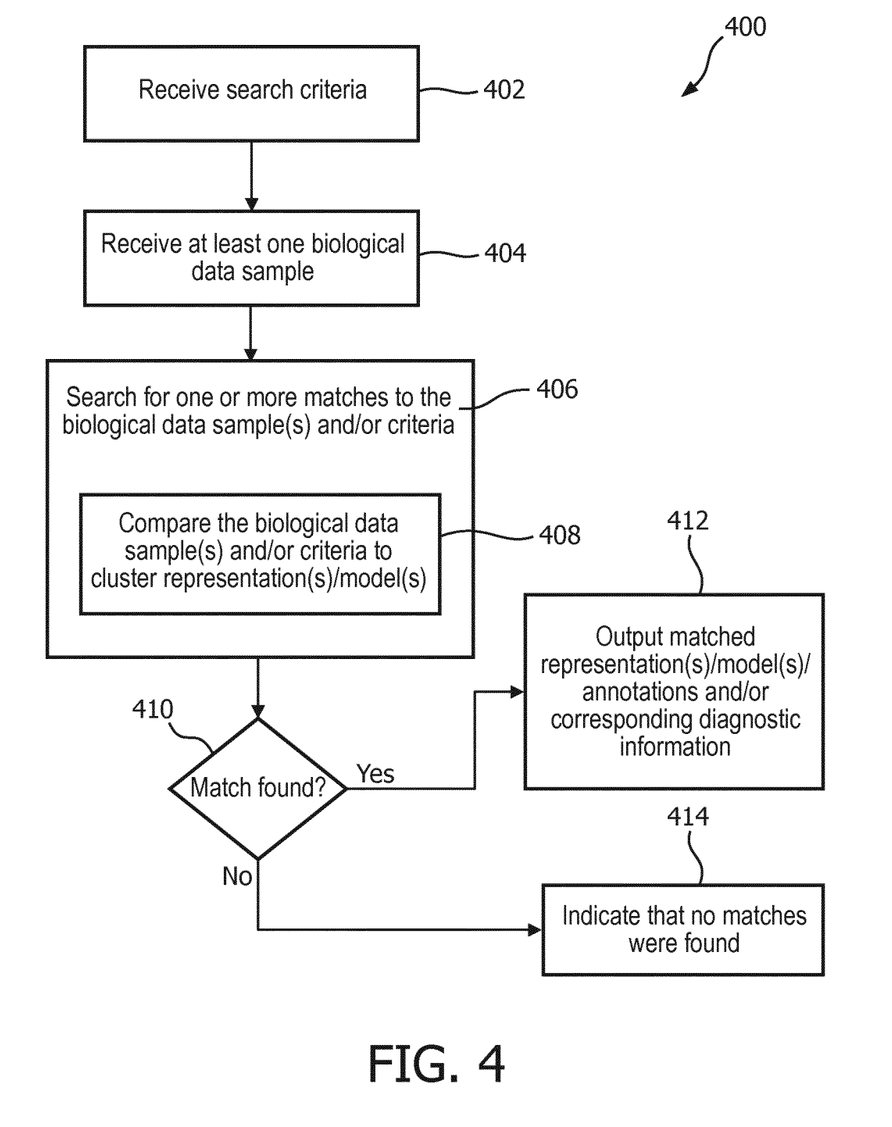
FIG. 4 is a high-level block/flow diagram of method 400 for providing diagnostic information in accordance with exemplary embodiments.

Referring to FIG. 4, with continuing reference to FIGS. 1 and 2, a method 400 for providing diagnostic information in accordance with exemplary embodiments is illustratively depicted. It should be noted that the method 400 can be combined with the method 200. Further, the method 400 can be performed to inform a health care provider of the particular feature data that should be compiled to obtain diagnostic information and, additionally or alternatively, can be performed to provide the diagnostic information to a health care provider. For example, the method 400 can begin at optional step 402 at which the system pre-processor 110 can optionally receive search criteria from a user through the user-interface 102 and can store the criteria in the storage medium 108. For example, the search criteria can denote a particular disease or subtype and/or a particular drug or other treatment that a health care provider is considering to prescribe to a patient. The search criteria received at step 402 can be entered alone for purposes of determining which feature data the healthcare provider should obtain from a patient to obtain diagnostic information. Alternatively, the search criteria can be entered with biological data. For example, at optional step 404, the pre-processor 110 can receive at least one biological data sample from a user through the user-interface 102 and store the sample in the storage medium 108. The biological data sample can be biological data formulated as a matrix, as discussed above with respect to step 202, and can be composed of an entire genome of a patient or constituent, or can be composed of a subset of genes and/or any set or subset of proteomic data discussed above. For example, the gene subset can be GS1 or GS2 discussed above, and can include corresponding biological data, such as, for example, the biological data included in matrix (1), above. Step 404 can also be performed with or without step 402. For example, if both step 402 and step 404 are performed such that the pre-processor 110 receives both search criteria and biological data sample(s), the pre-processor 110 can associate the criteria with the biological data and can store the criteria and biological data in the storage medium 108. Providing search criteria with the data samples can restrict a search for diagnostic information to a specific type of clinical variable, outcome or label. For example, the search can be restricted to diagnostic information related to a particular subtype and/or drug. Alternatively, step 404 can be performed without step 402 to enable a health care provider to obtain all information that is relevant to the biological data sample submitted to the system 106.

At step 406, the diagnostic matcher 126 can retrieve the search criteria and/or biological data sample(s) from the storage medium 108 and can search for one or more matches to the search criteria and/or biological data sample(s) within a database stored in storage medium 108. For example, at step 408, the diagnostic matcher 126 can compare the search criteria to annotations stored in the storage medium 108. For example, the diagnostic matcher can compare the search criteria to clinical variables, clinical outcomes and/or clinical labels stored and associated with cluster representations in a database in storage medium 108. The clinical variables, clinical outcomes and/or clinical labels stored and associated with cluster representations can be the annotations mapped at step 222. Similarly, the diagnostic matcher 126 can compare the biological data received at step 404 to centroids or other mathematical representations or models generated at step 224 of the method 200 and stored in the database in storage medium 108. In addition, if search criteria and biological data are received at steps 402 and 404, the diagnostic matcher 126 can filter the cluster representations and search through only cluster representations that are associated with the search criteria.

At step 410, the diagnostic matcher 126 can determine whether any match or matches to the search criteria and/or the biological data sample(s) is found. Here, any of a variety of semantic-based search methods can be employed to implement the searching and matching at steps 406 and 410 with respect to the search criteria. Similarly, the biological data sample(s) can be matched to cluster representations by selecting a cluster representation that falls within a similarity threshold distance, which can be preset or can be set by search criteria received at step 402. For example, the diagnostic matcher 126 can, at comparison step 408, determine a Euclidean distance measure, a Manhattan distance measure, and/or some other appropriate measure, between the biological data sample received at step 404 and all of the cluster representations or a subset of the cluster representations stored in the storage medium 108, where the subset of cluster representations can be determined by filtering the representations with the search criteria, as discussed above. In response to determining that the biological data sample received at step 404 falls within a threshold distance to any one or more cluster representations, which can be centroids, as discussed above, the diagnostic matcher 126 determines that this or these representation(s) are matches to the biological data. Otherwise, in response to determining that the biological data sample received at step 404 does not fall within the threshold distance to any of the stored representations, the diagnostic matcher 126 determines that a match was not found.

If a match to the search criteria and/or the biological data was not found, then the method can proceed to step 414, at which the diagnostic matcher 126 can indicate through the display/output device 104 that no matches were found. Thus, the diagnostic matcher 126 can indicate that the database stored in storage medium 108 lacks particular diagnostic information and can prompt the user to run the method 200 with additional biological data to expand the database.

If a match to the search criteria and/or the biological data was found, then the method can proceed to step 412, at which the diagnostic matcher 126 can output representation(s)/model(s) matched to biological data sample(s) received at step 404, annotations, which can include, for example, clinical variables, clinical outcomes and/or clinical labels, matched to search criteria, and/or diagnostic information associated with the matched representations/model(s). For example, if, at step 402, a user enters search criteria, which can denote, for example, a particular disease or subtype and/or a particular drug or other treatment that a health care provider is considering to prescribe to a patient, without a biological data sample, then the diagnostic matcher 126 can output, through the display/output device 104, the feature data set and/or representation, such as, for example, a centroid, associated with the matched annotations. For example, if the user enters a particular cancer subtype, then the diagnostic matcher 126 can output a gene set and/or a protein set and corresponding genomic/proteomic information associated with the gene set/protein set in the matched representation, such as, for example, copy number variation data, gene expression data and/or gene methylation data. The output can inform the health care provider of the particular biological data that he or she should obtain to determine, using system 106, whether a patient has the subtype in the search criteria. In addition, if a health care provider enters one or more biological data samples and one or more cluster representation matches are found, the diagnostic matcher 126 can output a cancer subtype associated with the matched representation to inform the healthcare provider that the patient likely suffers from this particular subtype. Accordingly, in this way, for example, the system can help guide the clinical management of the patient. Further, if a health care provider enters one or more biological data samples and one or more cluster representations matches are found, the diagnostic matcher 126 can alternatively or additionally, output the clinical variables, such as drug treatments or other types of treatments, and the clinical outcomes associated with the matched representation(s). For example, the diagnostic matcher 126 can in this way notify the health care provider that previous patients in a cluster matching the health care provider's current patient were cured by or responsive to, or were not responsive to, a particular drug therapy. As such, the methods 200, 400 and system 106 can provide effective clinical guidance to the health care provider during therapy planning for the patient.

Figure 5:
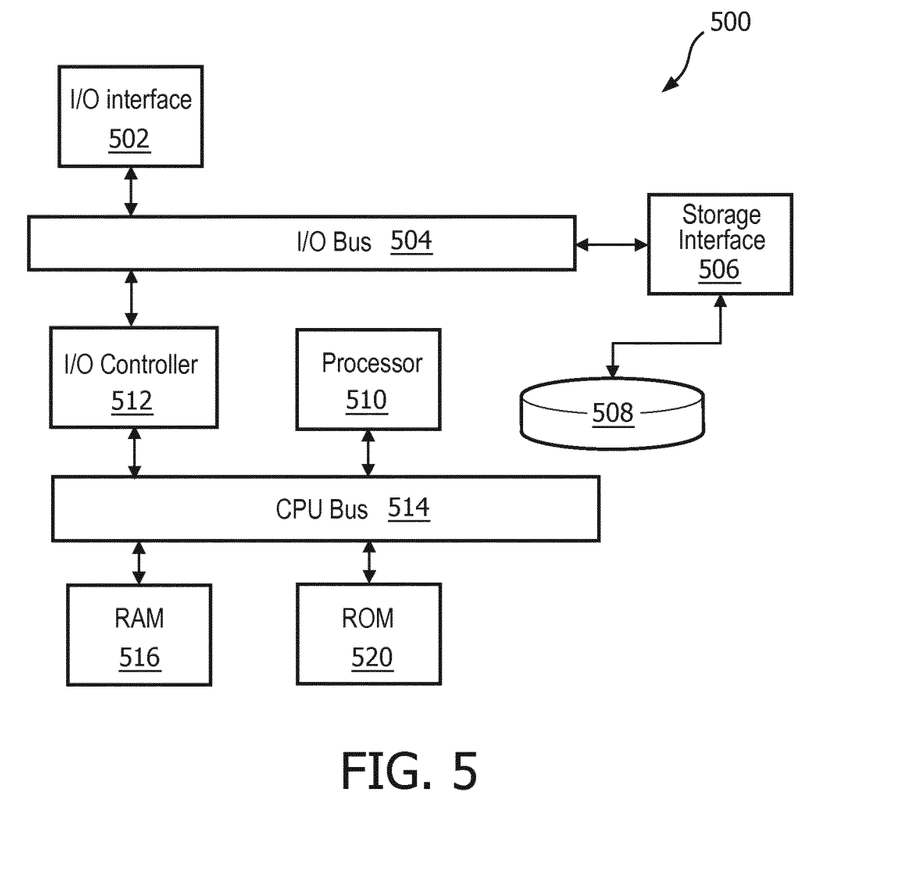
FIG. 5 is a high-level block/flow diagram of an exemplary computer system that can implement one or more exemplary embodiments.

Referring now to FIG. 5, an exemplary computing system 500 by which method embodiments of the present principles described above can be implemented, is illustrated. The computing system 500 includes a hardware processor or controller 510 and a storage medium 508. The processor 510 can access random access memory (RAM) 516 and read only memory (ROM) 520 through a central processing unit (CPU) bus 514. In addition, the processor 510 can also access the computer-readable storage medium 508 through an input/output controller 512, an input/output bus 504 and a storage interface 506, as illustrated in FIG. 5. The processor 510 can implement any one or more of elements 110, 126, 112, 122 or 124, or their sub-elements. The system 500 can also include an input/output interface 502, which can be coupled to a display/output device 104, the user-interface 102, a keyboard, a mouse, a touch screen, external drives or storage mediums, etc., for the input and output of data to and from the system 500. In accordance with one exemplary embodiment, the processor 510 can access software instructions stored in the storage medium 508 and can access memories 516 and 520 to run the software instructions stored on the storage medium 508. In particular, the software instructions can implement or be the steps of the method 200 and/or method 400. Alternatively, the software instructions that implement method 200 and/or 400 can be encoded in a computer-readable signal medium, such as a radio frequency signal, an electrical signal or an optical signal.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system for detecting patterns in constituents of at least one biological organism, said system being implemented by a user interface and at least one hardware processor and comprising:
    a data pre-processor of the at least one hardware processor configured to compile a first feature data set from at least one of genomic or proteomic data of the constituents of said at least one biological organism;
    a clustering module of the at least one hardware processor configured to:
        select multiple subsets of at least one of genes or proteins,
        identify clusters of said constituents from portions of the first feature data set corresponding to said selected subsets,
        compute membership values for said constituents indicating membership within said clusters, and
        perform an additional cluster determination process to obtain final clusters of constituents, wherein said additional cluster determination process clusters said constituents based on said membership values; and
    a representation generator of the at least one hardware processor configured to generate a visual representation of at least the final clusters of constituents, and further configured to output the generated visual representation to the user interface.

2. The system of claim 1, wherein said clustering module is further configured to iterate said additional clustering determination process to obtain said final clusters, wherein each iteration of said additional clustering determination process comprises determining other clusters of said constituents from an additional feature data set that is composed of at least a portion of preceding membership values determined from a preceding execution of said additional clustering determination process.

3. A method for detecting patterns in constituents of at least one biological organism, said method being implemented by a user interface and at least one hardware processor and comprising:
    receiving a dataset comprising at least one of genomic or proteomic data of the constituents of said at least one biological organism;
    compiling a first feature data set from the received at least one of genomic or proteomic data of the constituents of said at least one biological organism;
    selecting multiple subsets of at least one of genes or proteins;
    identifying said clusters from portions of the first feature data set corresponding to said selected subsets;
    computing membership values for said constituents indicating membership within said clusters;
    performing an additional cluster determination process to obtain final clusters of constituents, wherein said additional cluster determination process clusters said constituents based on said membership values;
    generating a visual representation of at least the final clusters of constituents; and
    displaying the generated visual representation via the user interface.

4. The method of claim 3, wherein said membership values are first membership values, wherein said performing comprises identifying second clusters of said constituents from a second feature data set that is composed of at least a portion of said first membership values and computing second membership values for said constituents indicating membership within said second clusters.

5. The method of claim 4, wherein said performing comprises selecting different subsets of said at least a portion of said first membership values and performing a cluster determination sub-process for each of said different subsets of said at least a portion of said first membership values to obtain said second clusters.

6. The method of claim 4, wherein said determining clusters of said constituents comprises forming said second feature data set by determining degrees of redundancy between clusters of said first clusters and pruning the membership values of at least one corresponding cluster of said first clusters having a respective degree of redundancy that is above a threshold.

7. The method of claim 4, further comprising:
    iterating said performing to obtain said final clusters, wherein each iteration of said performing comprises identifying other clusters of said constituents from an additional feature data set that is composed of at least a portion of preceding membership values determined from a preceding execution of said performing.

8. The method of claim 7, wherein at least one of said iterations of said performing comprises selecting different subsets of said at least a portion of preceding membership values and performing a cluster determination sub-process for each of said different subsets of said at least a portion of said preceding membership values.

9. The method of claim 8, wherein at least one of said iterations of said performing comprises forming a corresponding feature data set by determining degrees of redundancy between the other clusters and pruning the membership values of at least one corresponding cluster of said other clusters having a respective degree of redundancy that is above a threshold.

10. The method of claim 3, wherein said membership values denote probabilities of membership to corresponding clusters.

11. The method of claim 3, wherein at least one of said determining or performing comprises pruning said different subsets of at least one of genes or proteins based on cluster redundancy computations.

12. The method of claim 3, further comprising:
wherein said displaying comprises displaying at least one of clinical or phenotypic annotations to said final clusters.

13. The method of claim 12, wherein said annotations include at least one of drug response data, risk of recurrence of a disease or disease subtype data.

14. The method of claim 3, further comprising:
associating each of the final clusters with at least one of clinical variables, clinical outcomes or clinical labels;
receiving at least one biological data sample;
searching for at least one match to said at least one biological data sample by comparing said sample to representations of said final clusters; and
outputting the at least one of clinical variables, clinical outcomes or clinical labels associated with a representation of at least one of said final clusters matching said at least one biological data sample as diagnostic information.

15. A non-transitory computer-readable medium comprising a computer-readable program for execution by a processor, the non-transitory computer-readable medium comprising:
instructions for receiving a dataset comprising at least one of genomic or proteomic data of the constituents of said at least one biological organism;
instructions for compiling a first feature data set from the received at least one of genomic or proteomic data of the constituents of said at least one biological organism;
instructions for selecting multiple subsets of at least one of genes or proteins;
instructions for identifying clusters from portions of the first feature data set corresponding to said selected subsets;
instructions for computing membership values for said constituents indicating membership within said clusters;
instructions for performing an additional cluster determination process to obtain final clusters of constituents, wherein said additional cluster determination process clusters said constituents based on said membership values;
instructions for generating a visual representation of at least the final clusters of constituents; and
instructions for displaying the generated visual representation via the user interface.

16. The non-transitory computer-readable medium of claim 15, wherein said membership values are first membership values wherein said instructions for performing comprise instructions for identifying second clusters of said constituents from a second feature data set that is composed of at least a portion of said first membership values and instructions for computing second membership values for said constituents indicating membership within said second clusters.

17. The non-transitory computer-readable medium of claim 16, wherein said instructions for performing comprise instructions for selecting different subsets of said at least a portion of said first membership values and instructions for performing a cluster determination sub-process for each of said different subsets of said at least a portion of said first membership values to obtain said second clusters.

18. The non-transitory computer-readable medium of claim 16, wherein said instructions for determining clusters of said constituents comprise instructions for forming said second feature data set by determining degrees of redundancy between clusters of said first clusters and instructions for pruning the membership values of at least one corresponding cluster of said first clusters having a respective degree of redundancy that is above a threshold.

19. The non-transitory computer-readable medium of claim 16, further comprising:
instructions for iterating said performing to obtain said final clusters, wherein each iteration of said performing comprises identifying other clusters of said constituents from an additional feature data set that is composed of at least a portion of preceding membership values determined from a preceding execution of said performing.

20. The non-transitory computer-readable medium of claim 19, wherein at least one of said iterations of said performing comprises selecting different subsets of said at least a portion of preceding membership values and performing a cluster determination sub-process for each of said different subsets of said at least a portion of said preceding membership values.

* * * * *